United States Patent [19]

Kolb et al.

[11] 4,293,729
[45] Oct. 6, 1981

[54] ALKYLATION WITH DIB VAPOR ACID WASH

[75] Inventors: Norman P. Kolb, Overland Park, Kans.; Orlando Webb, Lee's Summit, Mo.

[73] Assignee: Stratford/Graham Engineering Corp., Kansas City, Mo.

[21] Appl. No.: 166,768

[22] Filed: Jul. 8, 1980

[51] Int. Cl.³ .............................................. C07C 3/54
[52] U.S. Cl. .................................... 585/715; 585/719; 585/730
[58] Field of Search ........................ 585/715, 719, 730

[56] References Cited

U.S. PATENT DOCUMENTS

| | | | |
|---|---|---|---|
| Re. 26,060 | 7/1966 | Nathan | 585/719 |
| 3,162,694 | 12/1964 | Beavon | 585/719 |
| 3,187,066 | 6/1965 | Nathan | 585/719 |
| 3,803,262 | 4/1974 | Goldsby | 585/730 |
| 4,128,597 | 12/1978 | Jones | 585/730 |
| 4,218,575 | 8/1980 | Webb | 585/719 |

Primary Examiner—Curtis R. Davis
Attorney, Agent, or Firm—Thomas M. Scofield

[57] ABSTRACT

Improvements in heat exchanging of distillation steps in sulfuric acid alkylation processes; removing water from the vaporous overhead fraction of a sulfuric acid alkylation process distillation step or deisobutanizer to enable mixing thereof with the vaporous hydrocarbon effluent from the reaction zone which contains sulfur dioxide vapors sulfur trioxide and $H_2SO_4$ mist, thus permitting mixing of the vaporous fraction and effluent for compression before use as a compressed heat exchanging medium in the alkylation process; sulfuric acid alkylation with deisobutanizer tower overhead effluent acid wash.

8 Claims, 2 Drawing Figures

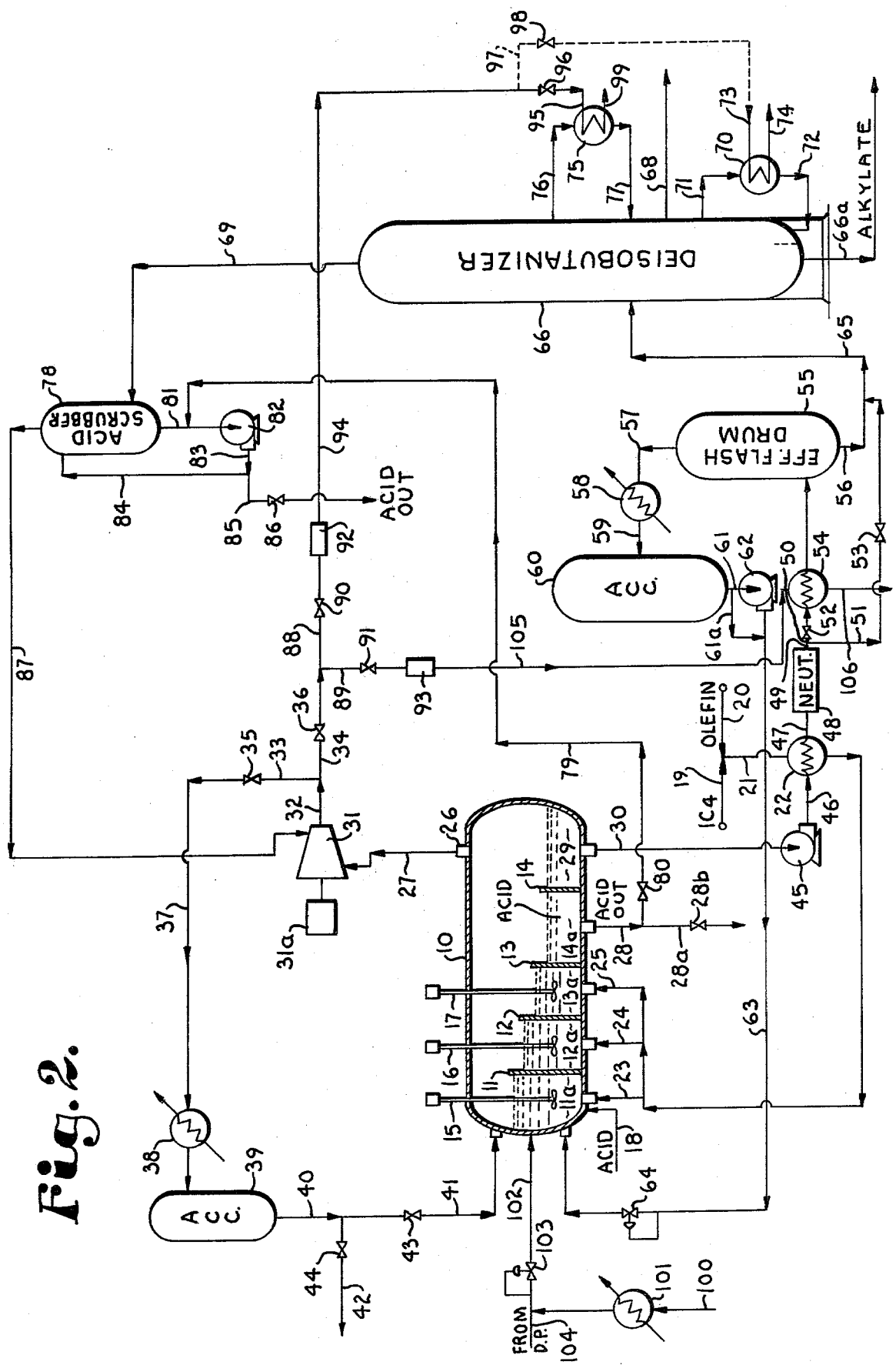

ALKYLATION WITH DIB VAPOR ACID WASH

BACKGROUND OF THE INVENTION

In sulfuric acid alkylation, an olefin is reacted with isobutane in excess in the presence of sulfuric acid catalyst. Although there are several variations of the alkylation process, for example, the Stratford effluent refrigeration system and the Kellogg autorefrigeration system, the effluent from the reaction system typically includes separated acid (which may be recycled to the reactor), a liquid hydrocarbon phase including alkylate product and a vaporous light hydrocarbon effluent. The latter may be directly from the reaction vessel as in the case of the Kellogg autorefrigeration system or from a suction trap-flash drum arrangement as in the Stratford effluent refrigeration system. The liquid hydrocarbon effluent is typically ultimately passed to a distillation zone from which a vaporous fraction is typically removed overhead, largely comprising excess isobutane and a liquid bottom fraction, particularly containing product alkylate, is also removed.

It has been proposed in the prior art to employ one or both of the vapor fractions from the reaction step and the distillation step, after compression, as a heat exchanging medium for the liquid hydrocarbon effluent, either with respect to an effluent flash system before the distillation step or of the distillation step itself. When these vaporous fractions are separately employed with separate compressors and circulation systems, with the different fractions being handled and recycled independently of one another, corrosion problems may not arise. However, when, as is most efficient, it is desired or attempted to use the two vaporous fractions from the reaction step and distillation as a common feed to a common compressor, before heat exchange, problems arise which have caused the development of the instant improvement.

With respect to the distillation of the liquid hydrocarbon effluent in the distillation tower or deisobutanizer, if this feed is not first neutralized, then, when the distillation tower is run at temperatures and pressures required to obtain the results necessary (even in a relatively low pressure tower), acidic components, present in the hydrocarbon phase effluent, when heated in the reboiler of the distillation or deisobutanizer tower, will decompose and foul the reboiler, preventing operation. In order, therefore, to provide practical operation of the distillation tower, the liquid hydrocarbon phase effluent necessarily must be neutralized (typically caustic and water wash) before reaching the distillation or DIB tower.

The result of the latter step is that the liquid hydrocarbon phase effluent, after the caustic treatment and water wash, will contain water or be wet. Inevitably, overhead isobutane vapors from the distillation tower will contain traces of water. When one considers that the reaction vaporous effluent, either from a suction trap-flash drum system or directly from an autorefrigeration reactor, is necessary dry and contains sulfur dioxide vapors, then it may be seen that the mixing of the distillation column wet overhead and the dry acidic reaction vaporous effluent will cause the formation in the mixture of highly corrosive weak acid. The use of such as a heat exchange medium in exchangers or reboilers will damage them and render them inoperative.

In the Stratford effluent refrigeration system, the suction trap-flash drum vapors are necessarily dry and acidic, because the hydrocarbons have been in contact with excess strong acid in the reaction phase and were separated in the acid settler without any water contamination or neutralization. Likewise, in the autorefrigeration system of Kellogg, the hydrocarbons, which have been in contact with excess strong acid in the reaction phase, are separated in their reaction vessel without any water contamination or neutralization. Should the overhead isobutane vapors from the distillation tower containing traces of water being mixed with the dry, acidic, sulfur dioxide containing vapors from the reaction side or system, the mixed vapors become very corrosive (weakly acidic). Thus, there is not only the likelihood or definite possibility of corrosion at the compressor itself, but also definite, unavoidable, necessary corrosion in the reboiler of the deisobutanizer tower or heat exchanger or condenser of an effluent flash vaporization system. Even where bauxite neutralization is employed, there remains a threat of water contamination of the DIB overhead vapors.

The present system makes it feasible to perform the necessary neutralization on the liquid hydrocarbon phase effluent before it is distilled in the deisobutanizer tower, but yet also permits the mixing, in a common compressor, of the normally incompatible reaction phase vapor effluent and distillation tower vapors overhead to provide a compressed heat exchanging medium which is not in any way corrosive, thereby protecting both the compressor and the reboiler of the distillation tower or whatever heat exchanger at which the combined, compressed light hydrocarbons may be employed.

PRIOR ART

Applicants are aware of the following prior art patents wherein light hydrocarbon vapors from the reaction step (Stratford effluent refrigeration suction trap-flash drum and Kellogg autorefrigeration reactor) and the distillation column (deisobutanizer) overhead are compressed and used as heat exchanging medium in parts of the alkylation systems such as the reboiler of the distillation tower and the heat exchanger of the effluent flash vaporization system:

Beavon U.S. Pat. No. 3,162,694, issued Dec. 22, 1964 for "Alkylation Process With Assisted Deisobutanizaing";

Nathan U.S. Pat. No. 3,187,066, issued June 1, 1965 for "Alkylation of Hydrocarbons";

Nathan U.S. Pat. No. Re. 26,060, reissued July 5, 1966 for "Alkylation of Hydrocarbons"; and Webb, O. U.S. patent application Ser. No. 894,996, filed Apr. 10, 1978, now U.S. Pat. No. 4,218,575, for "Alkylation Effluent Flash Vaporization With Heat Recovery".

BRIEF DESCRIPTION OF THE INVENTION

In a sulfuric acid alkylation process, an olefin is reacted with an excess of isobutane in the presence of a sulfuric acid catalyst. Either from the reaction vessel itself (as in the case of Kellogg autorefrigeration reactor) or from a suction trap-flash drum vessel associated with a Stratford effluent refrigeration reactor and the latter reaction vessel itself, there are provided a liquid hydrocarbon effluent containing alkylate product and a vaporous hydrocarbon effluent. Both of the these named effluent quantities are dry and acidic because the hydrocarbons have been in contact with excess strong acid in the reaction phase and separated either in the reactor or an acid settler without any water contamination or neutralization.

The liquid hydrocarbon effluent is first neutralized and then passed to a distillation zone wherein low boiling materials, particularly isobutane, are removed as a vaporous overhead fraction from the liquid alkylate product which is removed as bottoms from the distillation zone. Because of neutralization, typically involving caustic treatment and water wash, the overhead hydrocarbons from the distillation zone have traces of water therein. The water is removed from the distillation step or deisobutanizer overhead by means such as an acid scrubbing step, such optionally and preferably using spent acid taken off from the reaction step or acid settler recycle. The scrubber is employed even if bauxite neutralization is used to ensure the DIB overhead isobutane vapors are dry.

The vapors from the reaction side, being dry and acidic, then are mixed with the dry vapors from the overhead of the distillation tower in a common compressor and may be used as a heat exchange medium at critical points in the alkylation process, such as the distillation tower reboiler or heater for an effluent flash vaporization step.

While, theoretically, a bauxite neutralization process could provide a dry deisobutanizer overhead satisfactory for mixing with the dry, acidic reaction step vapors, in practice, such is not the case and, to accomplish the necessary step of having absolutely dependable, dry isobutane vapors returned to the common compressor, even if such bauxite neutralization process were employed, the DIB overhead dryer or acid scrubber has proved to be required.

OBJECTS OF THE INVENTION

A first object of the invention is to improve sulfuric acid alkylation processes wherein it is desired to utilize, in combination, light hydrocarbon vapors from the reaction side of the system and also from the overhead of the distillation tower compressed together for use as a heat exchanging medium to reboil the distillation tower or preheat an effluent flash distillation system or the like.

Another object of the invention is to provide efficient, absolutely dependable means of removing water from the overhead hydrocarbon vapors from a deisobutanizer tower, thereby to enable such to be used, in admixture, with the dry, acidic overhead vapors from an autorefrigerating reactor or a suction trap-flash drum system as a compressible heat exchanging medium.

Another object of the invention is to provide efficient, cheap, dependable means for removing water from the deisobutanizer tower overhead light hydrocarbon vapors, whereby the hydrocarbon phase effluent feed to said deisobutanizer tower may be neutralized without disabling such vapors from use in conjunction and admixture with dry, acidic vapors from the reaction side as a compressed heat exchanging medium.

Another object of the invention is to provide methods of and means for permitting full use of isobutane vapors from both the reaction and distillation sides of the sulfuric acid aklyation system as a compressed, combined heat exchanging medium, wherein there is no threat of clogging the reboiler with decomposed acidic components from a non-neutralized hydrocarbon feed to the DIB tower and no corrosion problem in use of the mixed compressible heat exchanging medium in reboilers, heat exchangers and compressors.

Other and further objects of the invention will appear in the course of the following description thereof.

THE DRAWINGS

In the drawings, which form a part of the instant specification and are to be read in conjunction therewith, embodiments of the invention are shown, particularly exemplified in schematic flow diagrams.

FIG. 2 is a schematic flow diagram of an alkylation reaction system wherein the reaction vessel is a Kellogg autorefrigeration type vessel, the subject improvement permitting the use in the same compressor of the light isobutane-containing hydrocarbons off the reaction vessel and the overhead from the deisobutanizer.

FIG. 2 STRUCTURE AND FUNCTION

Figure 1:
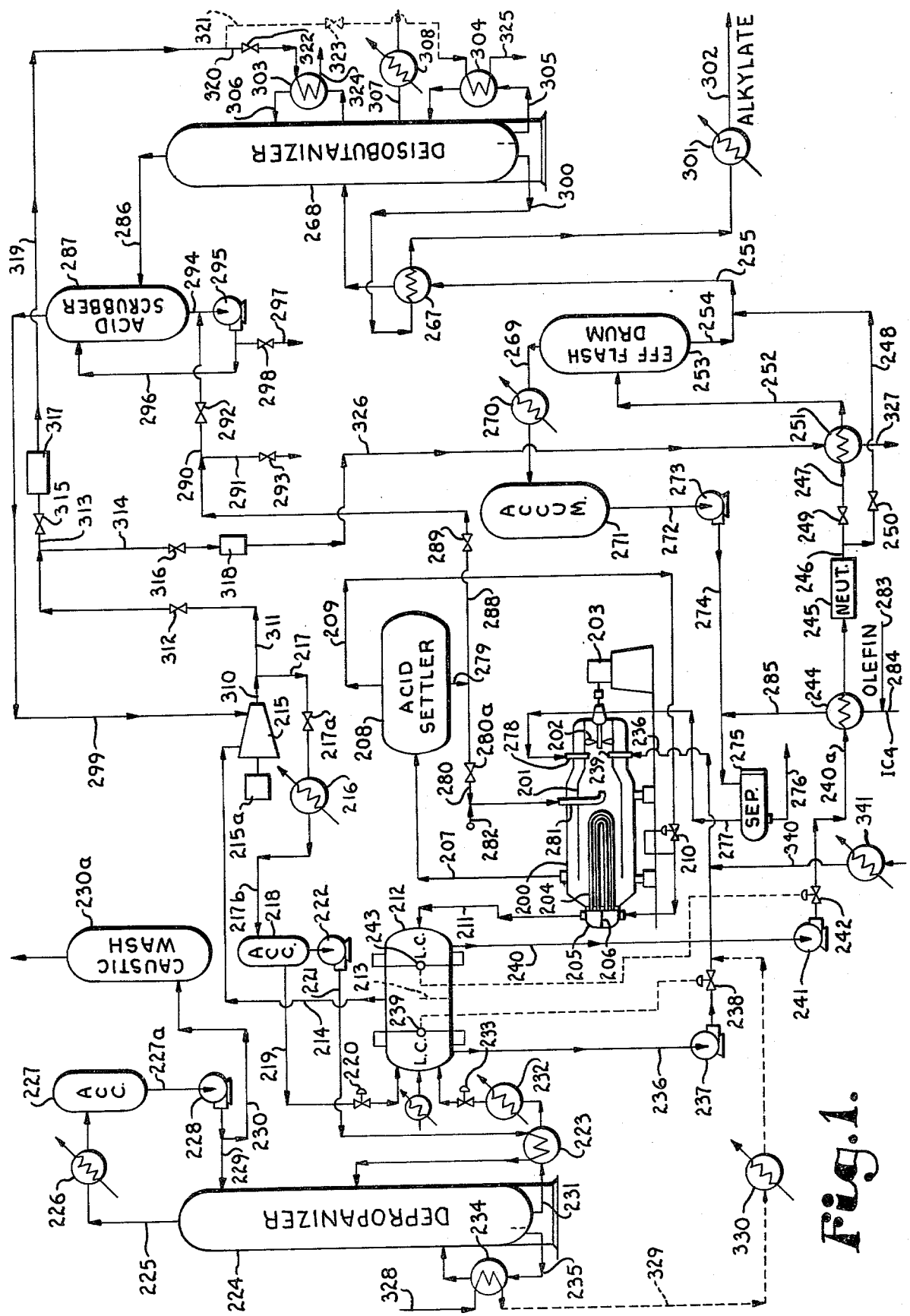
FIG. 1 is a schematic flow diagram of an alkylation process wherein the reaction step is carried out in a Stratford contactor and the reaction step is cooled by effluent refrigeration, the subject improvement permitting the use in a single compressor of the overhead isobutane vapors from the suction trap-flash drum vessel and the DIB tower.

Referring first to FIG. 2, therein is shown the subject improvement illustrated as applied to an autorefrigerated, cascade type reactor installation. At 10 is shown the reactor vessel having height graded baffles 11, 12, 13 and 14 which operate to define a series of cascade flow chambers, 11a, 12a, 13a and 14a therewithin. Mixers 15–17, inclusive agitate the liquid contents of the respective chambers. Flow line 18 supplies acid catalyst to chamber 11a. Fresh isobutane is supplied to the system through line 19 and olefin through line 20. Lines 19 and 20 join in a common line 21 which is heat exchanged at 22, the mixed isobutane and olefin being supplied to chambers 11–13a, inclusive through lines 23–25, inclusive. Flow control valves (not shown) preferably are provided on each of lines 23–25, inclusive. The alkylation reaction takes place in chambers 11a–13a, inclusive, with light hydrocarbon vapors evolved withdrawn from fitting 26 at the top of the vessel 10 through line 27. In chamber 14a, the acid settles and is taken out the bottom of the vessel through line 28. Spent acid is withdrawn from the system or recycled to line 18 through line 28a, valve controlled at 28b. The spillover of hydrocarbon effluent from chamber 14a is taken off the bottom of the vessel from chamber 29 through line 30.

The isobutane rich vapors taken off through line 27 pass to compressor 31 having driver 31a and therefrom to line 32 where the flow is selectively divided entirely between or split between lines 33 and 34 respectively controlled by valves 35 and 36. The vapors from line 27 are fed into an earlier (low pressure) stage of compressor 31, while the compressor at a later stage thereof (the compressor is multistage) is fed isobutane rich vapors from another source to be described.

Any compressor discharge flow through line 33 is passed via line 37 to condenser 38 and thence to accumulating vessel 39. Bottoms from accumulator 39, taken off through line 40, are split between lines 41 and 42 controlled by valves 43 and 44, respectively. Line 41 returns isobutane to the reactor and chamber 11a, while line 42 is a slipstream to a depropanizer (not seen). Valve 43 is preferably a back pressure valve.

The hydrocarbon effluent from chamber 29 passes through line 30 to pump 45, then through line 46 to heat exchanger 22, thereafter through line 47 to a neutralization steps schematically indicated at 48. The neutralization system may be a bauxite (dry) system or a more conventional caustic and water wash step (wet). Heat exchanger 22 operates to cool the isobutane and olefin input through line 21 to the reactor.

The output neutralization step 48 is in line 49, which splits into lines 50 and 51 controlled by valves 52 and 53, respectively. Line 50 passes to heat exchange at 54 and thence to effluent flash drum 55. Line 51 is a bypass of the entire effluent flash system and joins the bottoms withdrawal line 56 from drum 55. The manner of heat exchange at exchanger 54 will later be described in more detail.

At this point, suffice it to say that, due to heating at heat exchanger 54, isobutane rich vapors evolve from the net hydrocarbon effluent taken from chamber 29 through line 30. From effluent flash drum 55, line 57, off the top thereof, takes isobutane rich vapors, which condense at 58, and passes them via line 59 to accumulator drum 60. From accumulator 60, the condensed vapors are passed through line 61 and pump 62 into feed line 63 which leads into chamber 11a. Back pressure valve 64 may be employed on line 63 before input chamber 11a. Line 61a may be employed if pump 62 is not required.

The bottoms line 56 from drum 55, after optional joinder of bypass line 51, passes, through line 65, the partly isobutane relieved net hydrocarbon effluent to deisobutanizer tower 66. The presence of bypass line 51 is to show a standard (more conventional) passage for the hydrocarbon phase effluent from the reactor vessel to the deisobutanizer, specifically, omitting the effluent flash system just described. Typically, the entire hydrocarbon phase effluent will either go through the effluent flash system or pass around it, and is not split therebetween.

When the effluent flash system is used, providing the heat exchange step at 54, in connection with effluent flash drum 55, recycling light hydrocarbons back through condenser 58 and accumulator 60, there is achieved either initial reduction of the size of the deisobutanizer tower 66 in a new system or greater capacity of an existing system of this type which already has a deisobutanizer tower of afixed and given size. Accumulator 60 and/or pump 62 may not be necessary in some installations as, in many cases, the operative pressure of the effluent flash drum 55 will be high enough to force the condensate back to the reactor without requiring a pump, as by line 61a.

In the deisobutanizer tower 66, the net hydrocarbon effluent from chamber 29 of the autorefrigeration reactor 10 is distilled, less light fraction vapors removed in effluent flash drum 55, provided bypass line 51 is not employed. If the bypass line 51 is employed, the entire net hydrocarbon effluent is distilled. Normal butane, alkylate and other hydrocarbons heavier than butane charged as part of the feed stock may be withdrawn from the deisobutanizer through line 66a (bottoms line), depending upon the pressure maintained in the deisobutanizer. Alternatively, in more conventional fashion, normal butane may be withdrawn intermediate the height of tower 66 through line 68 (relatively higher pressure tower). Any remaining isobutane and other light paraffinic hydrocarbon vapors are taken overhead through line 69. Reboiling in conventional manner of deisobutanizer tower 66 is shown at heat exchanger 70 on the bottom of the tower having feed and recycle lines 71 and 72 and charge and removal lines 73 and 74 for the heat exchanging medium. A second, lower pressure reboiler is shown higher on the tower with heat exchanger 75 and input and recycle lines 76 and 77 thereto from the tower.

The light hydrocarbon (predominantly isobutane) vapors taken overhead through line 69 are passed through acid scrubber 78, wherein any traces of water whatsoever therein are removed. The acid feed to scrubber 78 comes from bleed line 79, valve controlled at 80, from acid withdrawal line 28 at acid chamber 14a in reactor 10. Line 79 joins scrubber bottoms withdrawal line 81 which passes to recycle pump 82, whose discharge line is 83. Recirculating acid for the scrubber is returned thereto via line 84, while acid is removed from the scrubbing system through line 85 valve controlled at 86. The dry isobutane vapors from the top of acid scrubber 78 are passed via line 87 to a later compression stage of compressor 31 from the input of line 27 due to pressure differences in the lines and source vessels.

Thus it may be seen that the dry isobutane vapors in line 87 may be mixed in compressor 31 with the dry, acidic vapors from reactor 10 without any hazard of creating weakly acidic, corrosive, wet vapors which will corrode heat exchangers. The sulfur dioxide vapors in the hydrocarbon line 27 have no water to mix therewith in the line 87 vapors and thus the admixture does not become corrosive.

The path, then, of compressed vapors discharged from compressor 31 into line 34 is to one or more points wherein the net liquid hydrocarbon phase effluent may be heated to evolve light isobutane vapors therefrom. The first one of these places is heat exchanger 54 before effluent flash drum 55. The second one of such places is a reboiler on the deisobutanizer tower 66.

Accordingly, compressed vapors in line 34 may pass into either (or both) line 88 or 89, valve controlled by valves 90 and 91, respectively. Optionally, but not necessarily, booster compressors may be supplied on either line at 92 or 93.

After booster 92 (if provided), line 94 passes to upper reboiler line 95, valve controlled at 96 or lower reboiler line 97, valve controlled at 98. These input lines pass, respectively, to heat exchangers 75 and 70, operative to reboil the contents of the deisbutanizer tower 66 at different levels thereof. Discharge lines 99 and 74 from heat exchangers 75 and 70 pass back to return line 100 having cooler 101 thereon and joining feed line 102 to chamber 11a of reactor 10. Back pressure valve 103 is provided on line 102.

In an alternative heat exchange of the liquid hydrocarbon phase effluent, line 105 (after booster compressor 93, if such is provided) passes to heat exchanger 54 before effluent flash drum 55 and thence through line 106 to join recycle line 100 prior to cooler 101.

In the autorefrigerated reaction vessel illustrated in FIG. 1, an important process equilibrium exists in the compartments of reactor 10. This equilibrium is effected by the olefin concentration in the acid in the compartment and the deisobutane concentration of the hydrocarbon liquid with which it is in contact. Since isoparaffinic hydrocarbon vaporization takes place directly from the reaction zones in chambers 11a, 12a and 13a, the only isobutane (other than makeup) available to increase the concentration of isobutane in the liquid and in contact with the catalyst is that which leaves the reactor as liquid effluent in line 30. Using a given deisobutanizer tower 66 and a given quantity of deisobutanizer overhead recycle, the effluent flash vaporization system shown accomplishes a considerable increase in isobutane concentration in the reaction and at the point of final equilibrium in the reactor, with the result that the yield and quantity of the alkylate product will be increased.

Thus it may be seen that a system has been provided wherein the net hydrocarbon phase effluent taken out line 30 may be neutralized before its passage to final distillation at 66 (in the system seen) yet wherein the normally wet isobutane vapors overhead from the deisobutanizer are dried so as to be mixable with the dry, acidic isobutane rich vapors within line 27. Consequently, but a single multiple stage compressor 31 may be employed to pressurize these compatible vapors and prepare same for heat exchange of the hydrocarbon phase effluent either at exchanger 54 or one of the reboilers 75 or 70 on the DIB tower 66. In this manner the most energy conservative use of the isobutane rich vapors in the alkylation system may be employed without any deterioration of the equipment such as by clogging of the deisobutanizer reboilers by unneutralized sulfur compounds or corrosion of the same reboilers or the effluent flash heat exchanger 54 by corrosive vapors from the compressor. Additionally, the compressor itself is protected from corrosion from admixture of the two vapors of different sources therein.

FIG. 1 EFFLUENT REFRIGERATION

Referring to FIG. 1, therein is shown a sulfuric acid alkylation process, apparatus array and system wherein a circulating reaction vessel of the Stratco contractor type is employed with indirect heat exchange thereof by effluent refrigeration of the reaction zone. In this figure, the numbering begins with 200 to avoid confusion with the description of FIG. 2.

Contactor 200, here shown as horizontal, has a circulating tube 201 with an impeller 202 at one end thereof driven by a power source 203. Tube bundle 204 extends from the header 205 which is divided centrally by plate 206. In vessel 200, olefinic hydrocarbons are alkylated with isoparaffinic hydrocarbons in the presence of sulfuric acid catalyst in conventional manner. Reaction effluent, comprising alkylate, excess isoparaffin hydrocarbons, polymeric acid contaminants and the like are taken off overhead through line 207 to acid settler 208. The hydrocarbon phase of the reaction effluent is taken off overhead from the settler through line 209 and passed to the input side of the tube bundle after back pressure valve 210. The latter maintains the reaction effluent under liquid phase conditions, as well as the reaction, per se and the cooling after expansion through valve 210 of the hydrocarbon phase of the reaction effluent, according to well established practice in effluent refrigeration, maintains the reaction zone temperature as desired.

From the upper portion of header 205, line 211 carries the hydrocarbon phase effluent, both liquid and vapor, to trap and flash drum 212. This vessel has a divider 213 centrally thereof which divides the liquids in the sides thereof, but permits communication thereover for vapor phase from both sides.

Vapor overhead from trap and flash drum 212, comprising light excess isoparaffinic hydrocarbons and normal paraffinic hydrocarbons, are taken off through line 214 and passed to the low pressure intake of compressor 215 driven by driver 215a. One line 217 from the compressor discharge is valve controlled at 217a and has condenser 216 thereon, line 217b leading to accumulator 218. Liquid from accumulator 218 may pass through line 219, back pressure controlled at valve 220, back to trap and flash drum 212. Alternatively, bottoms liquid is taken up through line 221 by pump 222 passing through heat exchange at 223 to depropanizer tower 224.

The overhead from tower 224 is taken off through line 225, passing to cooler 226 and thence to accumulator 227. Bottoms from accumulator 227 may return to tower 224 through line 229 or go out of the system through line 230 with an optional caustic wash step 230a. Pump 228 on line 227a drives the bottoms fluid from accumulator 227 through lines 229 and 230, which are valve controlled (not shown). Bottoms from depropanizer tower 224 are returned through line 231 through heat exchanger 222 and cooling step 232 as well as valve 233 to the bottom of trap and flash drum 212. Reboiling of depropanizer 224 takes place at exchanger 234 via line 235.

Liquid bottoms from the left hand side of trap and flash drum 212 are returned and handled with respect to the alkylation reaction and associated systems via line 236, pump 237 and valve 238 controlled by level control 239. Line 236 returns the trap bottoms, largely comprising unreacted isoparaffinic hydrocarbons, via input nozzle 239 at reactor 200 to a position interior of the circulating tube before propeller 202.

From the right hand side of barrier 213 in the trap and drum 212, bottom liquids are returned to the system via line 240 through pump 241 and valve 242 controlled by level control 243. From valve 242, the trap bottoms are passed via line 240a through heat exchange at 244 to an optional neutralization step at 245. This neutralization step may be a conventional caustic and water wash step (wet) or a bauxite neutralization (dry).

After neutralization step 245, line 246 divides into lines 247 and 248 valve controlled at 249 and 250, respectively. The contents of line 247 are heat exchanged at 251 in a manner to be described, leading into an effluent flash vaporization system, while line 248 acts as a bypass of the entire effluent flash vaporization system, if desired. Line 252 leads to effluent flash drum 253.

Bottoms from drum 253 are taken off via line 254 which, after it is joined by line 248, becomes common line 255. The contents of line 255 pass through heat exchange at 267 to deisobutanizer 268. The overhead from effluent flash drum 253 is taken off by line 269, condensed at 270 and passed through accumulator 271. Liquid from accumulator vessel 271 is removed therefrom via line 272, driven by pump 273 (if necessary) and thence passed via line 274 to water separator 275. From the latter vessel, water is taken out of the system via line 276, the output from separator vessel 275 via line 277 going to input fitting or nozzle 278 which feeds the contents of line 277 ahead of impeller 202 within circulating tube 201.

Referring back to acid settler 208, the acid recycle is via line 279 which splits into two lines, one of them, line 280, recycling acid to contactor 200 and acid input nozzle 281. New acid may be added to the system through line 282. Olefinic hydrocarbons are input to the system through line 283, this line joined by line 284 supplying new isoparaffinic hydrocarbons. The common line 285, after heat exchange at 244, joins line 274 before water separator 275.

The overhead from deisobutanizer tower 268 is taken off through line 286 and passed to acid scrubber 287. The acid supply to scrubber 287 is from bleed line 288, valve controlled at 289 as is line 280 at 280a. Line 288 splits into lines 290 and 291, valve controlled at 292 and 293. Acid may be taken out of the system through line 291. The acid supplied to the scrubber is through line 290 which joins bottom line 294 from scrubber 287. Pump 295 supplies acid in recycle line 296 to the top of scrubber 287, while spent acid may be withdrawn from the system through line 297, valve controlled at 298.

The new water free overhead of the deisobutanizer 268 is passed via line 299 from scrubber 287 to a later compressor stage at compressor 215 than the input from line 214 thereto. The bottoms from deisobutanizer 268 are taken off through line 300, heat exchanged at 267 (heating the contents of line 255), cooled at 301 and passed out of the system via line 302. This is the alkylate product. Reboilers 303 and 304 are provided, as conventional, for the upper and lower portions of tower 268, having feed and recycle lines 305 and 306 therefor, respectively. Depending upon the conditions of tower 268, normal butane may be taken off the tower at 307, and cooled or condensed at 308 to be removed from the system.

The use of the combined light hydrocarbon vapor effluent compressed in compressor 215 to heat exchange the liquid hydrocarbon phase effluent in the system will now be described.

The path of compressed vapors discharged from compressor 215 into line 310 is to one or more points wherein the net liquid hydrocarbon phase effluent (as particularly seen in line 240) may be heated to evolve light hydrocarbon (predominantly isobutane) vapors therefrom. The first one of these places is heat exchanger 251 before effluent flash drum 253. The second one of such places is a reboiler on the deisobutanizer tower 268.

Returning to compressor 215, the discharge therefrom (unless some is sent into line 217) is into line 311, valve controlled at 312. Line 312 divides into two lines, 313 and 314, each valve controlled at 315 and 316, respectively. Optional booster compressors on these lines, generally not needed, are seen at 317 and 318. Both of these boosters may be present or only one of them, depending upon the circumstances of heat exchange desired at the alternative locations.

From valve 315 and booster compressor 317 (if present) line 319 passes to the deisobutanizer 268, splitting into lines 320 and 321, valve controlled at 322 and 323, respectively. Line 320 is directed to reboiler 303 on an upper portion of the deisobutanizer 268, the cooled and condensed, light hydrocarbon heat exchanging medium exiting the boiler through line 324. Alternatively or also, line 321 passes the compressed vapor heat exchanging medium into reboiler 304 on the bottom of deisobutanizer tower 268, the cooled, condensed heat exchanging medium being passed therefrom through line 325.

As the other alternative heat exchange, after optional booster compressor 318, line 326 passes to heater 251 on line 247 to heat and drive off isobutane vapors from the net hydrocarbon effluent before same reaches effluent flash drum 253. The cooled, condensed heat exchanging vapors are taken off through line 327.

Heat is supplied at 234 via line 328 by steam or a bleed line from compressor 215. In the latter case, the condensed vapors, after cooling at 330 join line 236.

After heat exchange, lines 324, 325 and 327, join line 340 with cooler 341 thereon joining line 236 feeding reactor 200.

Thus it may be seen, as was previously described with respect to FIG. 1 and the autorefrigeration system therein, by virtue of use of acid scrubber 287, the single multiple stage compressor 215 may be employed to pressurize the compatible isobutane rich vapors from the suction trap and flash drum 212 and line 214 and from the deisobutanizer 268, after acid scrubbing, in line 299. The compressed, hot vapors then may be used as heat exchange of the hydrocarbon phase effluent either at exchanger 251 in the effluent flash system or one or both of the reboilers 303 or 304 on tower 268.

In the manner described, the most energy conservative use of the deisobutane rich vapors available in the alkylation system of FIG. 1 may be employed without any deterioration of the equipment, such as by clogging of the deisobutanizer reboilers by nonneutralized sulfur compounds or corrosion of the same reboilers from the exchange medium being used in them or the effluent flash heat exchanger 251, such by corrosive vapors from the compressor. Yet further, the compressor itself is protected from corrosion in all its parts which would be caused from admixture of the vapors from two different sources in line 214 and 299 absent the presence of acid scrubber 287 on line 286.

From the foregoing, it will be seen that this invention is one well adapted to attain all of the ends and objects hereinabove set forth together with other advantages which are obvious and which are inherent to the process.

It will be understood that certain process features, steps and sub-combinations thereof are of utility and may be employed without reference to other features, steps and process subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

We claim:

1. In a sulfuric alkylation process, wherein an olefin is reacted with isobutane in the presence of sulfuric acid catalyst in the reaction zone to produce a liquid hydrocarbon effluent containing the alkylate product and a vaporous hydrocarbon effluent, the liquid hydrocarbon effluent is first neutralized and then passed to a distillation zone wherein low boiling material are removed as a vaporous fraction from the liquid alkylate product and the liquid alkylate product is removed from the distillation zone, the vaporous hydrocarbon effluent having sulfur dioxide vapors therein and the vaporous fraction from the distillation zone having some water therein, the improvement which comprises:

first removing the water from the said vaporous fraction, passing the vaporous hydrocarbon effluent and water free vaporous fraction to a common compressor, compressing the said vaporous hydrocarbon effluent and vaporous fraction in the said common compressor in admixture with one another and thereafter passing the compressed mixture in heat exchanging relationship with the liquid hydrocarbon phase effluent whereby to heat same in order to drive off light hydrocarbons therefrom.

2. A process as in claim 1 wherein the said common compressor is multistage and the vaporous hydrocarbon effluent is passed through an earlier stage of the compressor than the vaporous fraction because of the lower pressure of the former when it reaches the compressor.

3. A process as in claim 1 wherein the compressed admixture is employed to heat exchange the distillation zone.

4. A process as in claim 1 wherein the compressed admixture is used to heat exchange the liquid hydrocarbon phase effluent before it reaches the distillation zone in an effluent flash vaporization system.

5. A process as in claim 1 wherein the water is removed from the vaporous fraction by passing said vaporous fraction through an acid scrubber before it is passed to the common compressor.

6. A process as in claim 5 wherein the acid for the scrubber is spent acid from the reaction stage.

7. A process as in claim 1 wherein the vaporous admixture is compressed to a pressure at which the temperature is above the boiling point of the isobutane in the liquid hydrocarbon effluent and below the boiling point of the alkylate product therein.

8. A process as in claim 1 wherein at least a part of the compressed admixture is condensed during the heat exchanging relationship with the liquid hydrocarbon phase effluent and passing at least a portion of the resulting condensate in the form in which it is produced to the alkylation reaction zone under the conditions employed therein.

* * * * *